United States Patent [19]

Freeland et al.

[11] Patent Number: 5,019,066
[45] Date of Patent: May 28, 1991

[54] ABSORBENT ARTICLE HAVING A WAISTPANEL

[75] Inventors: Mary E. Freeland, Norwood; Ted L. Blaney, West Chester, both of Ohio

[73] Assignee: The Proctor & Gamble Company, Cincinnati, Ohio

[21] Appl. No.: 353,923

[22] Filed: May 18, 1989

[51] Int. Cl.⁵ .......................................... A61F 13/15
[52] U.S. Cl. ................................................ 604/385.2
[58] Field of Search ................ 604/385.1, 385.2, 392, 604/396

[56] References Cited

U.S. PATENT DOCUMENTS

| | | |
|---|---|---|
| 3,978,861 | 9/1976 | Schaar . |
| 3,990,450 | 11/1976 | Schaar . |
| 3,995,640 | 12/1976 | Schaar . |
| 4,157,719 | 6/1979 | De Woskin .................... 604/385.2 |
| 4,397,645 | 8/1983 | Buell ................................ 604/380 |
| 4,425,128 | 1/1984 | Motomura ..................... 604/385.2 |
| 4,578,071 | 3/1986 | Buell ................................ 604/379 |
| 4,636,207 | 1/1987 | Buell . |
| 4,657,539 | 4/1987 | Hasse . |
| 4,681,580 | 7/1987 | Reising et al. ................. 604/385.1 |
| 4,743,246 | 5/1988 | Lawson . |
| 4,753,646 | 6/1988 | Enloe . |
| 4,778,458 | 10/1988 | Gronostajski ................... 604/366 |
| 4,880,421 | 11/1989 | Widlund .......................... 604/389 |
| 4,883,707 | 11/1989 | Newkirk ...................... 604/370 X |
| 4,900,317 | 2/1990 | Buell .............................. 604/370 |
| 4,938,757 | 7/1990 | Van Gompel et al. .......... 604/396 |

*Primary Examiner*—Randall L. Green
*Assistant Examiner*—David H. Willse
*Attorney, Agent, or Firm*—Steven W. Miller; Richard C. Witte

[57] ABSTRACT

A unitary disposable absorbent article such as a diaper is provided with an absorbent core; a liquid impervious backsheet; a liquid pervious topsheet; and a waistpanel positioned over and joined to said topsheet adjacent at least one of the end edges of the absorbent article. The waistpanel provides a waist feature that reduces the potential of liquids to wick between the skin of the wearer and the topsheet, reduces the potential for rollover of the waist portion of the absorbent article, and provides a soft, skin friendly, breathable waist feature.

20 Claims, 1 Drawing Sheet

ABSORBENT ARTICLE HAVING A WAISTPANEL

FIELD OF THE INVENTION

The present invention relates to absorbent articles such as disposable diapers, incontinent briefs, training pants, and the like, and more particularly, to absorbent articles having waist features.

BACKGROUND OF THE INVENTION

The major function of absorbent articles such as disposable diapers and adult incontinent briefs is to absorb and contain body exudates. Such articles are thus intended to prevent body exudates from soiling, wetting, or otherwise contaminating clothing or other articles, such as bedding, that come in contact with the wearer. A common mode of failure for such products occurs when body exudates leak out of the gaps between the article and the wearer's waist to adjacent clothing because they are not immediately absorbed within the article.

Contemporary disposable diapers have a topsheet, a backsheet, an absorbent core, elasticized leg flaps, and a waist feature such as a waistshield or an elasticized waistband to improve both wearing comfort and the ability to contain body exudates. These waist features prove effective generally to prevent wicking and overflow from the diaper to clothing contacting the edges of the diaper adjacent the waist of the wearer at low loadings of liquids. Despite the effectiveness of such structures, however, body exudates can leak through the waist portion of the diaper and soil the wearer's clothing at relatively high loadings of liquids.

Leakage of liquids from the waist portion of the diaper is enhanced by the tendency of the waist portion of the diaper to rollover and sag during use. The waist portion will thus not maintain contact with the body of the wearer thereby allowing large gaps to be formed between the wearer and the diaper that allow clothing or other articles to contact the interior of the diaper such that liquids can more easily wick out of the diaper.

Further, waist features for diapers are typically formed from liquid impervious materials to contain liquids within the absorbent core of the structure and to protect the wearer's garments from soiling. These materials are perceived as being hot and uncomfortable when placed against the skin of the wearer. Further, the impermeability of the materials typically relates not only to liquids but also to gases such as air and water vapor. The inability of vapors or air to pass through the impervious materials impedes the self-drying of the diaper which could occur by the evaporation of liquids contained within the diaper and leads to the hot and sticky feelings of the wearer.

Therefore, it is an object of the present invention to provide an absorbent article which has an improved waist feature.

It is also an object of the present invention to provide an absorbent article having a waist feature which reduces the potential of liquids to wick to the edge of the article in the waist portion.

It is a further object of the present invention to provide an absorbent article with a waist feature which reduces the potential for rollover of the waist portion.

It is a still further object of the present invention to provide an absorbent article having a waist feature which reduces gapping in the waist portions of the absorbent article.

It is an additional object of the present invention to provide an absorbent article having a soft, skin friendly, breathable waist feature.

These and other objects of the present invention will be more readily apparent when considered in reference to the following description and when taken in conjunction with the accompanying drawings.

SUMMARY OF THE INVENTION

In accordance with the present invention, a unitary disposable absorbent article such as a diaper is provided with a waistpanel to enhance the fit of the diaper about the wearer's waist, the containment of liquids within the diaper, and the breathability of the diaper. The diaper generally comprises a liquid pervious topsheet, a liquid impervious backsheet associated with the topsheet, an absorbent core having side edges and waist edges, a waist flap extending outwardly beyond the waist edges of the absorbent core; and a waistpanel disposed adjacent at least one, and preferably adjacent each, of the end edges of the diaper.

BRIEF DESCRIPTION OF THE DRAWINGS

While the specification concludes with claims particularly pointing out and distinctly claiming the subject matter which is regarded as forming the present invention, it is believed that the invention will be better understood from the following descriptions which are taken in conjunction with the accompanying drawings in which like designations are used to designate substantially identical elements, and in which:

DETAILED DESCRIPTION OF THE INVENTION

Figure 1:
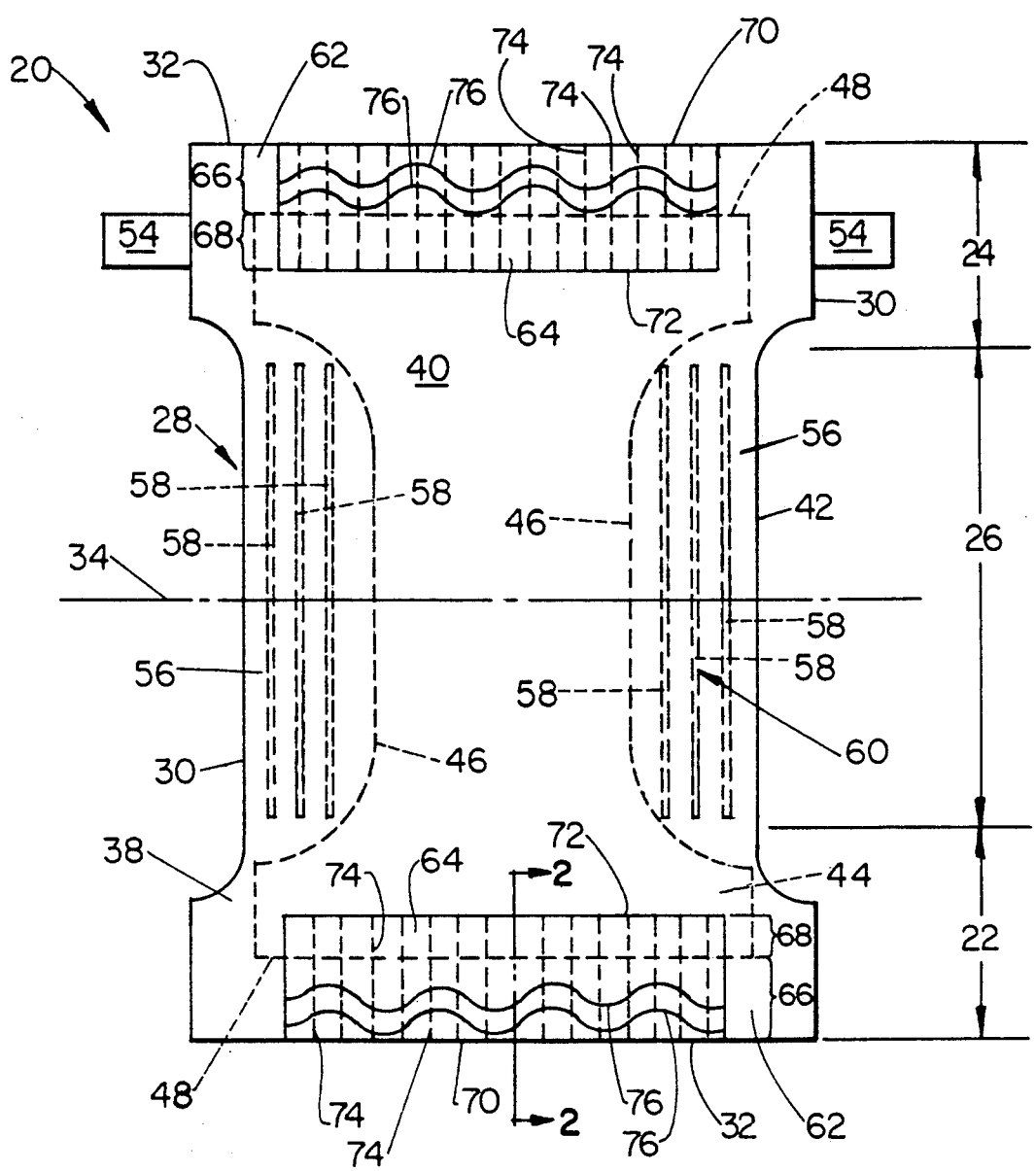
FIG. 1 is a plan view of a disposable diaper embodiment of the present invention having portions cut-away to reveal underlying structure.

As used herein, the term "unitary disposable absorbent article" refers to articles which absorb and contain body exudates and more specifically refers to articles which are placed against or in proximity to the body of the wearer to absorb and contain the various exudates discharged from the body, which are intended to be discarded after a single use (i.e., they are not intended to be laundered or otherwise restored or reused), and which are unitary in that they do not require separate manipulative parts like a separate holder and liner. A preferred embodiment of the unitary disposable absorbent article of the present invention, diaper 20, is shown in FIG. 1. As used herein, the term "diaper" refers to a garment generally worn by infants and incontinent persons that is worn about the lower torso of the wearer. It should be understood, however, that the present invention is also applicable to other unitary disposable absorbent articles such as incontinent briefs, undergarments, training pants, and the like.

FIG. 1 is a plan view of the diaper 20 of the present invention in its flat-out, uncontracted state (i.e., with all elastic induced contraction pulled out) with portions of the structure being cut-away to more clearly show the construction of the diaper 20 and with the portion of the diaper 20 which contacts the wearer facing the viewer. The diaper 20 is shown in FIG. 1 to have a front waist region 22, a back waist region 24, a crotch region 26, and a periphery 28 which is defined by the outer edges of the diaper 20 in which the longitudinal edges are designated 30 and the end edges are designated 32. The diaper 20 additionally has a lateral centerline which is designated 34.

The diaper 20 comprises a liquid pervious topsheet 38, the liquid-receiving surface of the diaper 20 being generally defined by the topsheet 38 and being designated 40; a liquid impervious backsheet 42; an absorbent core 44 having side edges 46 and waist edges 48; a pair of tape tab fasteners 54; elasticized leg cuffs 60 each preferably comprising a side flap 56 and one or several elastic members 58; a waist flap 62 extending outwardly from and along each waist edge 48 of the absorbent core 44; and a waistpanel 64 having an outward portion 66 and an inward portion 68.

FIG. 1 shows a preferred embodiment of the diaper 20 in which the topsheet 38 and the backsheet 42 have length and width dimensions generally larger than those of the absorbent core 44. The topsheet 38 and the backsheet 42 extend beyond the edges of the absorbent core 44 to thereby form the periphery 28 of the diaper 20. The periphery 28 defines the outer perimeter or, in other words, the edges of the diaper 20. The periphery 28 comprises the longitudinal edges 30 and the end edges 32.

The diaper 20 has a front waist region 22 and a back waist region 24 extending, respectively, from the end edges 32 of the diaper periphery 28 toward the lateral centerline 34 of the diaper 20 a distance of at least about 1/10, preferably from about ¼ to about ⅓ the length of the diaper 20. The waist regions comprise those portions of the diaper 20 which, when worn, encircle the waist of the wearer. The crotch region 26 is that portion of the diaper 20 between the front waist region 22 and the back waist region 24, and comprises that portion of the diaper 20 which, when worn, is positioned between the legs of the wearer and covers the lower torso of the wearer.

Figure 2:
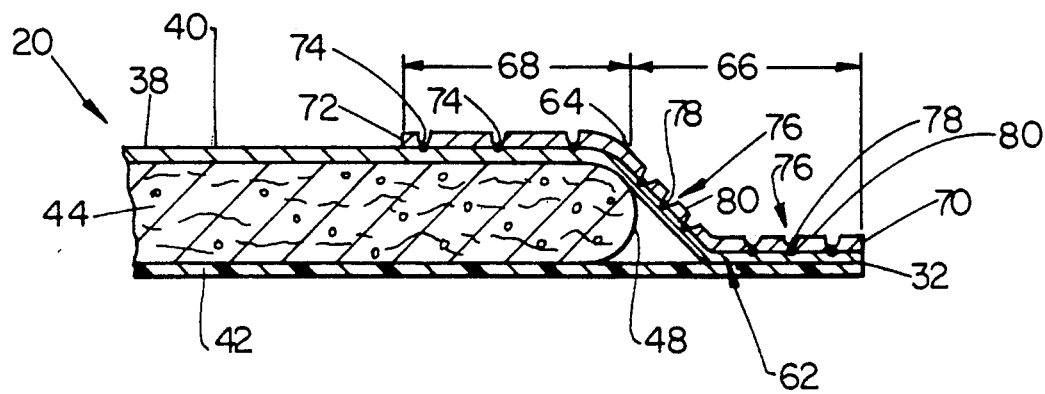
FIG. 2 is a fragmentary sectional view taken along section line 2—2 of FIG. 1.

FIG. 2 is a fragmentary sectional view taken along line 2—2 of FIG. 1 and depicts the preferred diaper construction in the front waist region 22 of the diaper 20. (It should be understood that the diaper construction in the back waist region 24 is preferably similar or identical to the construction described with respect to the front waist region 22 except that the length or width of the waistpanels may be different to accommodate the particular diaper design or the placement of the tape tab fasteners 54 in the back waist region 24 or other reasons. For example, the waistpanel positioned in the front waist region may be wider than that waistpanel positioned in the back waist region 24 so that the latter will not interfere with the tape tab fasteners 54. Further, the waistpanel positioned in the back waist region 24 need not be as long as the waistpanel positioned in the front waist region 22.) The absorbent core 44 is disposed between the topsheet 38 and the backsheet 42; the topsheet 38 and the backsheet 42 preferably extending beyond the waist edge 48 of the absorbent core 44 to form the waist flap 62. The backsheet 42 is secured to the absorbent core 44 and to the topsheet 38 in the waist flap 62 by attachment means (not shown) as are known in the art. The waistpanel 64 is formed by a separate piece of material positioned over and joined to the portion of the topsheet 38 forming the waist flap 62 and a portion of the topsheet 38 that overlies the absorbent core 44. The waistpanel 64 has a first lateral edge 70, a second lateral edge 72, an inward portion 68, and an outward portion 66. The outward portion 66 comprises that portion of the waistpanel 64 extending from the waist edge 48 of the absorbent core 44 toward and preferably to the end edge 32 of the diaper 20. The first lateral edge 70 is preferably joined to the topsheet portion of the waist flap 62 adjacent the end edge 32 of the diaper 20 by panel securement means 74. The inward portion 68 is contiguous with the outward portion 66. The inward portion 68 comprises that portion of the waistpanel 64 extending longitudinally toward the center of the diaper (lateral centerline 34) from the waist edge 48 of the absorbent core 44. The second lateral edge 72 is joined to the topsheet 38 by the panel securement means 74. Thus, at least the first lateral edge 70 and the second lateral edge 72 are joined to the topsheet 38. The waistpanel is preferably provided with antiwicking segments 76, each comprising a compacted portion 78 and an uncompacted portion 80.

The topsheet 38 overlays a major portion of the absorbent core 44 so that exudates that are discharged onto the topsheet 38 readily penetrate through the topsheet 38 where they are absorbed by the absorbent core 44. The topsheet 38 extends outwardly toward the edges of the absorbent core 44 so that a major portion of the absorbent core 44 is disposed between the topsheet 38 and the backsheet 42. In the preferred embodiment shown in FIG. 1, the topsheet 38 has length and width dimensions generally larger than those of the absorbent core 44.

The topsheet 38 may be substantially noncoterminous with the backsheet 42 in the waist flap 62 so that liquids will not wick through the topsheet 38 underneath and beyond the waistpanel 64, thereby reducing the wicking of liquids out of the diaper 20. The topsheet 38 would extend toward the edges of the absorbent core 44, preferably beyond the waist edges 48, wherein the topsheet 38 terminates inwardly of the first lateral edge 70 of the waistpanel 64. Inwardly is used herein to denote configurations wherein the terminating edge of the topsheet 38 is positioned adjacent the first lateral edge (i.e., the topsheet 38 is substantially coterminous with the first lateral edge) and configurations wherein the terminating edge of the topsheet 38 is positioned remotely from and inboard of the first lateral edge. Adjacent is used in this context to mean that the topsheet terminates at the first lateral edge, minus small areas of topsheet material that may extend inside the first lateral edge due to machine tolerances during manufacture or variations in the topsheet's area when it is manufactured. In the embodiments shown in FIG. 2, the topsheet 38 is positioned adjacent the first lateral edge and is secured to the backsheet 42 adjacent to the first lateral edge by edge attachment means (not shown) so as to form a leakage-resistant seal along the end edges 32 of the diaper 20.

The topsheet 38 is compliant, soft feeling, and nonirritating to the wearer's skin. Further, the topsheet 38 is liquid pervious permitting liquids to readily penetrate through its thickness. A suitable topsheet 38 may be manufactured from a wide range of materials such as porous foams, reticulated foams, apertured plastic films, natural fibers (e.g., wood or cotton fibers), synthetic fibers (e.g., polyester, polyethylene or polypropylene fibers) or from a combination of natural and synthetic fibers.

A preferred topsheet 38 comprises staple length polypropylene fibers having a denier of about 1.5 such as Hercules Type 151 polypropylene marketed by Hercules, Inc. of Wilmington, Del. As used herein, the term "staple length fibers" refers to those fibers having a length of at least about 15.9 mm (0.625 inches), typically about 38 mm to about 48 mm.

There are a number of manufacturing techniques which may be used to manufacture the topsheet 38. For example, the topsheet 38 may be woven or nonwoven. Methods of making nonwovens include that the material may be spunbonded, meltblown, carded, or the like. A preferred topsheet 38 is carded, and thermally bonded by means well known to those skilled in the fabrics art. Preferably, the topsheet 38 has a basis weight from about 15 to about 25 grams per square meter. The percentage of the fibers bonded together is typically between about 18% and about 28%. A relatively lower density topsheet than the waistpanel 64 is preferred to assist in preventing wicking of liquids to the end edge 32.

The absorbent core 44 may be any means which is generally compressible, conformable, non-irritating to the wearer's skin, and capable of absorbing and retaining liquids and certain body exudates.

The absorbent core 44 may be manufactured in a wide variety of sizes and shapes (e.g., rectangular, hourglass, asymmetric, etc.) and from a wide variety of liquid absorbent materials commonly used in disposable diapers and other absorbent articles, such as comminuted wood pulp which is generally referred to as airfelt. Examples of other suitable absorbent materials include creped cellulose wadding, absorbent foams, absorbent sponges, superabsorbent polymers, absorbent gelling materials, or any equivalent materials or combination of materials. The total absorbent capacity of the absorbent core 44 should, however, be compatible with the design exudate loading and the intended use of the diaper 20. Further, the size and absorbent capacity of the absorbent core 44 may be varied to accommodate wearers ranging from infants through adults.

An exemplary embodiment of the absorbent core 44 comprises a layer of absorbent material comprising hydrophilic fibers and particles of absorbent gelling material (hydrogel) such as the absorbent structure described in U.S. Pat. No. 4,610,678 entitled "High-Density Absorbent Structure" which issued to Paul T. Weisman and Steven A. Goldman on Sept. 9, 1986, and which patent is incorporated herein by reference. An alternative embodiment of the absorbent core 44 is a dual-layered absorbent core in a preferred configuration such as is generally described in U.S. Pat. No. 4,673,402 entitled "Absorbent Article With Dual-Layered Cores" which issued to Paul T. Weisman, Dawn I. Houghton and Dale A. Gellert on June 16, 1987, and which is incorporated herein by reference, having an asymmetric-shaped upper layer and a lower layer. A particularly preferred embodiment of an absorbent core 44 useful in the present invention is described in allowed U.S. patent application Ser. No. 06/887,584 filed on July 18, 1986, by Miguel Alemany and Charles J. Berg; allowed Dec. 20, 1988; Batch No. 088; which discloses absorbent members having a storage zone and an acquisition zone having a lower average density and a lower average basis weight per unit area than the storage zone so that the acquisition zone may effectively and efficiently rapidly acquire discharged liquid. This allowed U.S. patent application is hereby incorporated herein by reference.

A preferred embodiment of the diaper 20 has a modified hourglass-shaped absorbent core 44 and is intended to be worn by infants ranging in weight from about 5 kgs to about 12 kgs (about 12 pounds to about 26 pounds). It should be understood, however, that the size, shape, configuration, and total absorbent capacity of the absorbent core 44 may be varied to accommodate wearers ranging from infants through adults. Therefore, the dimensions, shape, and configuration of the absorbent core 44 may be varied (e.g., the absorbent core 44 may have a varying caliper, or a hydrophilic gradient, or may contain absorbent gelling materials). The absorbent core 44 is preferably a batt of airfelt and particles of absorbent gelling material about 32 cm wide (lateral dimension), about 45 cm long (longitudinal dimension) and approximately 7 cm across the narrowest part of the crotch region 26.

The backsheet 42 is positioned adjacent the absorbent core 44 and is preferably attached thereto by attachments means (not shown) such as those well known in the art. For example, the backsheet 42 may be secured to the absorbent core 44 by a uniform continuous layer of adhesive, a patterned layer of adhesive, or an array of separate lines or spots of adhesive. Adhesives which have been found to be satisfactory are manufactured by Eastman Chemical Products Company of Kingsport, Tenn. and marketed under the tradename Eastobond A-3 and by Century Adhesives, Inc. of Columbus, Ohio and marketed under the tradename Century 5227.

The backsheet 42 is impervious to liquids and is preferably manufactured from a thin plastic film, although other flexible liquid impervious materials may also be used. The backsheet 42 prevents the exudates absorbed and contained in the absorbent core 44 from wetting articles which contact the diaper 20 such as bedsheets and undergarments. Preferably, the backsheet 42 is a polyethylene film having a thickness of from about 0.012 mm (0.5 mil) to about 0.051 mm (2.0 mils), although other flexible, liquid impervious materials may be used. As used herein, the term "flexible" refers to materials which are compliant and which will readily conform to the general shape and contours of the human body.

Suitable polyethylene films are manufactured by Ethyl Visqueen, a division of Ethyl Corporation and marketed in the trade as Film No. 4009, and by the Monsanto Chemical Corporation and marketed in the trade as Film No. 8020. The backsheet 42 is preferably embossed and/or matte finished to provide a more clothlike appearance. Further, the backsheet 42 may permit vapors to escape from the absorbent core 44 while still preventing exudates from passing through the backsheet 42.

The size of the backsheet 42 is dictated by the size of the wearer and the exact diaper design selected. In a preferred embodiment, the backsheet 42 has a modified hourglass shape extending beyond the absorbent core 44 a minimum distance of at least about 1.3 cm to about 2.5 cm (about 0.5 to about 1.0 inch) around the entire diaper periphery 28.

Tape tab fasteners 54 are typically applied to the back waist region 24 of the diaper 20 to provide a fastening means to hold the diaper 20 on the wearer. The tape tab fasteners 54 can be any of those well known in the art, such as the fastening tape disclosed in U.S. Pat. No. 3,848,594 entitled "Tape Fastening System For Disposable Diaper" issued to Kenneth B. Buell on Nov. 19, 1974, which is incorporated herein by reference. These tape tab fasteners 54 or other diaper fastening means are typically applied near the top edge of a diaper 20 in its "in-use" configuration.

The side flaps 56 are that portion of the diaper 20 between the periphery 28, the longitudinal edges 30, and the side edges 46 of the absorbent core 44. The waist flaps 62 are that portion between the periphery 28, the end edges 32, and the waist edges 48 of the absorbent core 44. Thus, in a preferred embodiment of the present invention as shown in FIG. 1, the side flaps 56 are formed from the extension of the backsheet 42 and the topsheet 38 from and along the side edges 46 of the absorbent core 44 in at least the crotch region 26 and the waist flaps 62 are formed from the extension of the backsheet 42 and the topsheet 38 from and along the waist edges 48 of the absorbent core 44.

Leg cuffs 60 are disposed adjacent one or both, preferably each, of the longitudinal edges 30 of the diaper 20 to enhance the containment of exudates in the leg regions of the wearer. The leg cuffs 60 may comprise any of several means as are well known in the diaper art. An exemplary embodiment of a leg cuff comprises a side flap 56 and one or more elastic members 58 as is described in detail in U.S. Pat. No. 3,860,003, entitled "Contractable Side Portions for Disposable Diaper" which issued to Kenneth B. Buell on Jan. 14, 1975, which is incorporated herein by reference. An alternative leg cuff construction comprises a barrier cuff and spacing means with or without a gasketing cuff such as is described in detail in U.S. Pat. No. 4,808,147 entitled "Disposable Absorbent Article Having Elasticized Flaps Provided With Leakage Resistant Portions" which issued to Mohammed I. Aziz and Ted L. Blaney on Jan. 3, 1989, and U.S. Pat. No. 4,695,278 entitled "Absorbent Article Having Dual Cuffs" which issued to Michael I. Lawson on Sept. 22, 1987, both of which patents are incorporated herein by reference.

A waistpanel 64 is provided adjacent each end edge 32 of the diaper 20 from which it is desired to reduce waist flap 62 rollover and gapping, and to provide a soft, skin friendly member that enhances breathability of the diaper and containment of body exudates.

In the description that follows, reference will be made to a waistpanel 64 disposed adjacent the end edge 32 of the diaper 20 in both the front waist region 22 and the back waist region 24 of the diaper 20. While this is a preferred construction, it is possible that a waistpanel may be disposed in only one of either the front waist region 22 or the back waist region 24. When a waistpanel is present in only one waist region of the diaper 20, it is preferably disposed in the front waist region 22 since sagging and gapping is most acute in the front waist region 22 and since most of the urine is deposited into the diaper 20 toward the front waist region 22, especially at night if the wearer is lying down on their stomach.

Each waistpanel 64 is a separate element joined to at least the waist flap 62. The term "integral waistpanel" refers to a waistpanel 64 which is a discrete separate element joined to the waist flap 62. Thus, the waistpanel 64 is not formed from other elements of the diaper 20. Preferably, a single piece of material serves as the waistpanel 64, although several pieces of material may be used to form the waistpanel 64.

Referring to FIG. 2, it can be seen that each waistpanel 64 has a first lateral edge 70, a second lateral edge 72, an outward portion 66 and, preferably, an inward portion 68.

The outward portion 66 of the waistpanel 64 extends from the waist edge 48 of the absorbent core 44 toward and preferably to the end edge 32 of the diaper 20. Without wishing to be bound by theory, it is believed that the outward portion 66 tends to reduce rollover of the waist flap 62 during use because it provides a stiff member that decreases the flexibility of the waist flap 62. The outward portion 66 may also act as a member that inhibits leakage of exudates beyond the waist edge 48 of the absorbent core 44 because the outward portion 66 inhibits liquids from wicking beyond the waist edge 48. The outward portion 66 also preferably forms a soft finished end edge for the diaper 20. In the preferred embodiment shown in FIG. 2, the outward portion 66 is positioned so that the first lateral edge 70 is positioned adjacent to the end edge 32 to form a segment of the end edge 32 of the diaper 20.

The inward portion 68 is contiguous with the outward portion 66 and extends from the waist edge 48 of the absorbent core 44 generally toward the center of the diaper (or the absorbent core) a distance sufficient to provide protection against liquids migrating from the absorbent core 44 through the waistpanel 64 and to retard the flow of liquids along the top surface 40 of the topsheet 38 and the capillary channels between the topsheet 38 and the skin of the wearer. It has been found that extending the inward portion 68 a distance of from about 3 mm to about 45 mm (about 0.125 inch to about 1.75 inches), preferably from about 30 mm to about 45 mm (about 1.25 inches to about 1.75 inches), more preferably about 38 mm (1.5 inches), longitudinally inward from the waist edge 48 generally towards the center of the absorbent core 44 is sufficient to provide such protection. In an alternative embodiment of the present invention, the inward portion 68 extends from the waist edge 48 toward the center of the absorbent core 44 from about 3 mm to about 25 mm (about 0.125 inch to about 1 inch), preferably from about 6 mm to about 12 mm (about 0.25 inch to about 0.5 inch).

Each waistpanel 64 is positioned over and joined to the waist flap 62, preferably to the topsheet 38. As used herein, the term "joined" encompasses configurations whereby the waistpanel 64 is directly affixed to the waist flap 62 (topsheet 38), and configurations whereby the waistpanel 64 is indirectly affixed to the waist flap 62 (topsheet 38) by affixing the waistpanel 64 to an intermediate member or members which are in turn affixed to the waist flap 62 (topsheet 38). In the preferred embodiment, the waistpanel 64 and the topsheet 38 are joined directly to each other by panel attachment means 74 as are known in the art. The panel attachment means 74 may be adhesives, heat/pressure seals using heat/pressure sealing techniques as are known in the art, ultrasonic bonds using ultrasonic bonding techniques as are known in the art, or any other materials or methods as are known in the art. The panel attachment means 74 are preferably discrete ultrasonic bonds.

The panel attachment means 74 may comprise a variety of configurations. The panel attachment means 74 may comprise an array of discrete areas of joinder (bonding) along the width and/or length of the waistpanel 64. For example, the discrete areas may comprise a multiplicity of spaced dots, circles, dashes or ovals arranged in either a random or regular pattern. Alternatively, the panel attachment means 74 may comprise a multiplicity of lines or a continuous or patterned layer of joinder. An example of configurations for adhesively bonding the waistpanel 64 to the topsheet is described in U.S. Pat. No. 4,573,986 entitled "Disposable Waste-Containment Garment" which issued to James A. Minetola and David R. Tucker on Mar. 4, 1986, and is incorporated herein by reference. The panel attachment means 74 are preferably formed by ultrasonically bonding the waistpanel 64 to the topsheet 38 in a regularly spaced pattern of discrete dots along both the length and width of the waistpanel 64.

At least both the first lateral edge 70 and the second lateral edge 72 are joined to the topsheet. Both edges are joined to the topsheet 38 so that the waistpanel 64 will lie against the topsheet 38. It is desired that the waistpanel 64 not be able to be spaced away from the liquid-receiving surface 40 of the topsheet 38. While at least the lateral edges are joined to the topsheet 38, it is preferable to join other portions of the bottom surface of the waistpanel 64 to the topsheet 38 so that the waistpanel 64 cannot be easily separated from the topsheet 38. Most preferably, the waistpanel 64 is joined to the topsheet 38 along its entire length and width.

The width of the waistpanel 64 may vary depending upon the thickness and cost of the material that forms the waistpanel. The width of the waistpanel 64 will typically be greater than or equal the width of the waist edge 48 of the absorbent core 44 with configurations possible whereby the width of the waistpanel 64 is equal to the width of the diaper 20 at the end edge 32. Alternatively, the width of the waistpanel 64 could be less than the width of the absorbent core 44 measured at the waist edge 48. In this embodiment, the width of the waistpanel 64 would preferably be greater than about 50%, more preferably between about 60% and about 95%, of the width of the absorbent core 44 at the waist edge 32.

The waistpanel 64 can have varying shaped surface areas and cross-sectional areas. For example, the waistpanel 64 can have a rectangular, square, trapezoidal, elliptical or diamond shaped surface area. The cross-sectional area of each waistpanel 64 may be rectangular, square, pyramidal, or any other cross-sectional areas as may be known in the art. Rectangular shaped surface areas and cross-sectional areas are preferred.

In order to break the wicking capillaries between the skin of the wearer and the topsheet 38, the waistpanel 64 must be a relatively thick material so that the upper surface of the waistpanel 64 and the skin of the wearer are held above the plane (the liquid-receiving surface 40) of the topsheet 38 when the wearer is lying on the waistpanel 64. Generally, the compressed thickness or caliper of the waistpanel 64 should be at least about 0.075 mm (about 0.003 in), more preferably from about 0.1 mm to about 1.0 mm, and most preferably from about 0.2 mm to about 0.6 mm. The compressed caliper (caliper under a relatively high load) is measured using a standard gauge with the sample under a load of about 35 $g/cm^2$ (0.5 psi). These thickness variations provide that the upper surface of the waistpanel 64 should be above the liquid-receiving surface 40 of the topsheet 38. Each waistpanel 64 also preferably has an initial thickness or caliper (caliper under a relatively low load) of at least about 0.25 mm (about 0.01 in), preferably between about 0.25 mm and about 1.5 mm, most preferably between about 0.35 mm and about 1.0 mm. The initial caliper is measured using a standard gauge with the sample under a load of 10 $g/cm^2$.

The compressed density of the material forming the waistpanel 64 should preferably be between about 0.02 $g/cm^3$ and about 0.2 $g/cm^3$, more preferably between about 0.04 $g/cm^3$ and about 0.15 $g/cm^3$, and most preferably between about 0.04 $g/cm^3$ and about 0.10 $g/cm^3$. The compressed density of the waistpanel is calculated from its basis weight and the compressed caliper as defined above. The basis weight is measured by cutting a certain size sample and weighing the sample on a standard scale, the weight and area of the sample determining the basis weight.

The waistpanel 64 may be formed from a variety of materials which provide the function described herein. Materials similar to those used for the topsheet 38 are generally suitable for use as the waistpanel 64. Each waistpanel 64 is manufactured from soft and flexible webs of material that are compliant, soft feeling, and non-irritating to the skin of the wearer so that the waistpanel may be positioned against the skin of the wearer. Thus, the waistpanel 64 may be manufactured from materials such as foams, apertured plastic films, natural fibers (e.g., wood or cotton fibers), synthetic fibers (e.g., polyester or polypropylene fibers) or from a combination of natural and synthetic fibers. There are also a number of manufacturing techniques which may be used to manufacture the waistpanel 64, including, for example, that the waistpanel 64 may be woven or nonwoven. As used herein, the term "nonwoven" includes any material which has been formed without the use of textile weaving processes which produce a structure of individual fibers which are interwoven in an identifiable manner. Methods of making suitable nonwovens include that the material may be spunbonded, meltblown, carded, or the like. If the waistpanel comprises a nonwoven material, the wicking properties of the material itself will affect the capability of the waistpanel 64 to prevent liquids from wicking through the waistpanel 64 to the end edge 32. Thus, a nonwoven material with a small wicking capability is preferred.

A preferred material for use as the waistpanel 64 is a thermally bonded, carded nonwoven material comprised of staple length polypropylene fibers having a denier of 2.2, such as Hercules Type 195 polypropylene, that has a basis weight of from about 20 $g/m^2$ to about 78 $g/m^2$, more preferably from about 25 $g/m^2$ to about 42 $g/m^2$. The denier of the fibers may be varied from about 2.2 to about 3. The percentage of the fibers bonded together is typically about 20% so that the structure has a high loft to provide a bulky material having high caliper. The waistpanel preferably has a compressed caliper of about 0.33 mm (0.013 in), an initial caliper of about 0.5 mm (0.02 in), and a compressed density of about 0.1 $g/cm^3$.

Alternatively, the waistpanel 64 may be formed from a laminate comprising at least a first layer and a second layer. For example, the first layer may comprise the above-specified nonwoven material laminated to another less thick nonwoven material or an apertured plastic film. Thus, at least the first layer must meet the targeted caliper and density ranges and not necessarily the composite material. Examples of suitable apertured plastic films are described in U.S. Pat. No. 3,929,135 entitled "Absorptive Structure Having Tapered Capillaries" issued to Hugh A. Thompson on Dec. 30, 1975; U.S. Pat. No. 4,342,314 entitled "Resilient Plastic Web Exhibiting Fiber-Like Properties" issued to Clifford J. Radel and Hugh A. Thompson on Aug. 3, 1982; U.S. Pat. No. 4,463,045 entitled "Macroscopically Expanded Three-Dimensional Plastic Web Exhibiting Non-Glossy Visible Surface And Cloth-Like Tactile Impression" issued to Nicholas A. Ahr, Paul R. Louis, William I. Mullane, Jr., and William R. Ouellette on July 31, 1984; and U.S. Pat. No. 4,629,643 entitled "Microapertured Polymeric Web Exhibiting Soft And Silky Tactile Impression" issued to John J. Curro and E. Kelly Linman on Dec. 16, 1986; all of which are incorporated herein by reference. If the second layer comprises a nonwoven, it could be laminated to the first layer on the surface opposite of the surface adjacent the liquid-receiving surface 40 of the topsheet 38 to provide a particularly skin friendly and soft material against the skin of the wearer. If the second layer comprises an apertured plastic film, the second layer would preferably be positioned between the topsheet and the first layer to enhance the containment of exudates within the absorbent core 44. The materials of the first layer and the second layer may be laminated together in any suitable manner as is known in the art to provide a waistpanel that is soft and pleasing to the wearer's skin.

The waistpanel 64 is preferably breathable to allow gas to readily penetrate through its thickness. In this specification, "breathable" is used to describe a material or element which is "permeable to vapor." The two terms can be and are used interchangeably. (It is recognized that virtually all sheet materials have some finite, albeit sometimes small, permeability to vapor and, under certain pressures, liquid.) As used in this specification, "permeable" is used to describe a material which allows a readily measurable passage of liquid or vapor, as the case may be, under the conditions normally prevailing during the use of the diapers.) Breathable, in the simplest terms, is freely permeable to vapor. The waistpanel 64 is also typically liquid permeable to allow liquids to readily penetrate through its thickness. In a more complex situation, a waistpanel may be relatively permeable to vapor but relatively impermeable to liquid.

The overall breathability of the waistpanel 64 (that is to say the amount of air and moisture vapor which can be transported through the waistpanel in any given length of time under any given conditions) can be varied and controlled by adjustment of a number of factors. Among these are the inherent permeability of the material used to construct the waistpanel 64, the caliper of the waistpanel 64, and the size of the waistpanel 64.

Further, the waistpanel 64 need not be breathable over its entire surface area. A portion of the surface area of the waistpanel 64, preferably the outward portion 66, may be vapor impermeable to prevent the passage of vapor beyond the absorbent core 44. In this alternative embodiment, at least a portion of, preferably from about 50% to about 95%, of the surface area of the waistpanel 64 is breathable.

As shown in FIGS. 1 & 2, the waistpanel 64 is preferably provided with anti-wicking segments 76. The anti-wicking segments 76 comprise a compacted portion 78 which alters the flow of liquid as it moves from the point of discharge towards the end edge 32 of the diaper 20. The desired effects of the compacted portion 78 may be achieved in many ways such as by filling the interspatial voids of the compacted portion with an adhesive or other liquid impermeable material. In this manner, the compacted portion is made to act as a barrier to the movement of liquid. In a preferred embodiment, however, the compacted portion 78 is compressed or densified relative to the other portions of the waistpanel 64, which portions for convenience are designated uncompacted portions 80. In other words, both the spacing between fibers and the interspatial void volume are reduced in the compacted portion 78 to an extent sufficient to cause the compacted portion 78 to exhibit a greater capillary attraction for liquid than the uncompacted portion 80. Thus, liquid contacting the compacted portion 78 will wick into and through the compacted portion 78. The compacted portion 78, therefore, alters the liquid flow pattern and by configuring the compacted portion 78 as hereinafter described, liquid is directed away from those portions of the diaper 20 from which leakage may occur.

The compacted portions 78 may take on a variety of configurations such as an array of discrete areas. For example, the array of discrete areas may comprise one or a multiplicity of spaced circles, dashes, or ovals arranged in either a random or regular pattern. Preferably, the compacted portion may comprise one or a multiplicity of bands or gaps or spaces arranged so that the gaps or spaces in adjoining lines do not coincide thereby providing a tortuous path from the point of liquid discharge to a point from which the liquid can wet the vicinity surrounding the diaper. Further, the compacted portion may comprise one or a multiplicity of continuous bands which may be rectilinear or curvilinear and which may have parallel side edges forming a band of uniform width or may have no parallel sides forming a band of varying width.

In the preferred embodiment illustrated in FIG. 2, the compacted portions 78 comprise a continuous curvilinear line positioned on the waistpanel 64 in the front waist region 22 and a multiplicity of continuous dots as provided in both the front waist region 22 and the back waist region corresponding to each of ultrasonic bond sites used in joining the waistpanel 64 to the topsheet 38. The dots are arranged in rows which are generally parallel to the end edge 32 and which traverse the entire width and length of the waistpanel 64.

The waistpanel 64 may alternatively be colored to enhance the opacity and aesthetics of the diaper 20. The waistpanel 64 may also have designs placed onto or embossed into it so as to improve aesthetics. Further, the waistpanel 64 may incorporate absorbent material to provide an additional absorbent structure to enhance containment of exudates.

The diaper 20 is applied to a wearer by positioning the back waist region 24 under the wearer's back and drawing the remainder of the diaper 20 between the wearer's leg so that the front waist region 22 is positioned across the front of the wearer. The ends of the tape-tab fasteners 54 are then secured preferably to outwardly facing areas of the diaper 20. In this manner, the waistpanel 64 should be disposed to provide the dispositions and functions described hereinbefore.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A unitary disposable absorbent article having longitudinal edges and end edges, the absorbent article comprising:
   a liquid pervious topsheet;
   a liquid impervious backsheet secured to said topsheet;
   an absorbent core disposed between said topsheet and said backsheet, said absorbent core having side edges and waist edges;

a waist flap extending from and along each of said waist edges of said absorbent core to form said end edges; and an integral waistpanel disposed adjacent at least one of the end edges of the absorbent article, said waistpanel being positioned over and joined to said topsheet and said waist flap so that the waistpanel is positioned against the skin of the wearer during use, said waistpanel having an outward portion extending from said waist edge of said absorbent core toward said end edge, an inward portion contiguous with said outward portion and extending from said waist edge toward the center of said absorbent core, a first lateral edge joined to said waist flap, and a second lateral edge joined to said topsheet, said waistpanel having a compressed caliper under a load of about 35 g/cm² of at least about 0.075 mm.

2. The absorbent article of claim 1 additionally comprising panel attachment means for joining said waistpanel to said topsheet along the entire length and width of said waistpanel.

3. The absorbent article of claim 2 wherein said panel attachment means comprises ultrasonic bonds.

4. The absorbent article of claim 1 wherein the width of said waistpanel is greater than or equal to the width of said absorbent core at said waist edge.

5. A unitary disposable diaper having longitudinal edges, end edges, a front waist region, a back waist region, and a crotch region positioned between the front waist region and the back waist region, the diaper comprising:

a liquid pervious topsheet;

a liquid impervious backsheet secured to said topsheet;

an absorbent core disposed between said topsheet and said backsheet, said absorbent core having side edges and waist edges;

a waist flap extending from and long each of said waist edges of said absorbent core to form said end edges, each of said waist flaps being formed from the extension of said topsheet and said backsheet beyond said waist edge; and an integral waistpanel disposed adjacent at least one of the end edges of the diaper, said waistpanel being positioned over and joined to said topsheet so that the waistpanel is positioned against the skin of the wearer during use, said waistpanel having an outward portion extending from said waist edge of said absorbent core to said end edge, an inward portion contiguous with said outward portion and extending from said waist edge toward the center of said absorbent core, a first lateral edge joined to said topsheet, and a second lateral edge joined to said topsheet, said waistpanel having a compressed caliper under a load of about 35 g/cm² of at least about 0.075 mm, and at least a portion of said waistpanel being breathable.

6. The diaper of claim 5 additionally comprising panel attachment means for joining said waistpanel to said topsheet along the entire length and width of said waistpanel.

7. The diaper of claim 6 wherein said panel attachment means comprises ultrasonic bonds disposed in an array of discrete areas of bonding.

8. The diaper of claim 7 wherein said array of discrete areas of bonding comprises a multiplicity of spaced dots.

9. The diaper of claim 7 wherein the initial caliper of said waistpanel under a load of 10 g/cm² is at least about 0.25 mm.

10. The diaper of claim 9 wherein between about 50% and about 95% of the surface area of said waistpanel is breathable.

11. The diaper of claim 9 wherein the entire surface area of said waistpanel is breathable.

12. The diaper of claim 11 additionally comprising at least one anti-wicking segment positioned on said waistpanel, said anti-wicking segment comprising a compacted portion and an uncompacted portion.

13. The diaper of claim 12 wherein said waistpanel is positioned in said front waist region.

14. The diaper of claim 12 wherein the width of said waistpanel is less than or equal to the width of said absorbent core at said waist edge.

15. The diaper of claim 14 wherein the width of said waistpanel is greater than about 50% of the width of said absorbent core at said waist edge.

16. A unitary disposable diaper having longitudinal edges, end edges, a front waist region, a back waist region, and a crotch region positioned between said front waist region and said back waist region, the diaper comprising:

a liquid pervious topsheet;

a liquid impervious backsheet secured to said topsheet;

an absorbent core disposed between said topsheet and said backsheet, said absorbent core having side edges and waist edges;

a waist flap extending from and along each of said waist edges of said absorbent core to form said end edges, each of said waist flaps being formed from the extension of said topsheet and said backsheet beyond said waist edge;

an integral waistpanel disposed adjacent each of said end edges of the diaper, said waistpanel being positioned over and directly affixed to said topsheet so that the waistpanel is positioned against the skin of the wearer during use, said waistpanel having an outward portion extending from said waist edge of said absorbent core to said end edge, an inward portion contiguous with said outward portion and extending from said waist edge toward the center of said absorbent core from about 3 mm to about 45 mm, said waistpanel being joined to said topsheet along its length and width, said waistpanel having a compressed caliper under a load of about 35 g/cm² of at least about 0.075 mm, the width of said waistpanel being less than the width of said absorbent core at said waist edge and greater than about 50% of the width of said absorbent core at said waist edge, and the entire surface area of said waistpanel being breathable; and panel attachment means for affixing said waistpanel to said topsheet, said panel attachment means comprising an array of discrete areas of joinder.

17. The diaper of claim 16 wherein the width of said waistpanel is between about 60% and about 95% of the width of said absorbent core at said waist edge.

18. The diaper of claim 17 wherein said panel attachment means comprises ultrasonic bonds comprising a multiplicity of spaced dots arranged in a regularly spaced pattern.

19. The diaper of claim 18 additionally comprising at least one anti-wicking segment positioned on each of said waistpanels, said anti-wicking segment comprising a compacted portion of a continuous curvilinear band, and uncompacted portions.

20. The diaper of claim 19 wherein said waistpanel comprises a nonwoven material formed from a carded, thermally bonded web of polypropylene fibers.

* * * * *